United States Patent [19]

Lantos

[11] 4,096,249

[45] Jun. 20, 1978

[54] TRIALKYLPHOSPHINEGOLD(I)-LOWER ALKYL CARBAMOYL GLUCOPYRANOSIDES

[75] Inventor: Ivan Lantos, Blackwood, N.J.

[73] Assignee: SmithKline Corporation, Philadelphia, Pa.

[21] Appl. No.: 769,147

[22] Filed: Feb. 16, 1977

[51] Int. Cl.$^2$ .................... A61K 31/70; C07H 11/04
[52] U.S. Cl. ................................. 424/180; 536/4; 536/117; 536/118; 536/121; 536/122
[58] Field of Search ............... 536/117, 118, 121, 122; 424/180

[56] References Cited

U.S. PATENT DOCUMENTS 3,635,945  1/1972  Nemeth et al. ............... 536/121

*Primary Examiner*—Johnnie R. Brown
*Attorney, Agent, or Firm*—Joan S. Keps; Richard D. Foggio; William H. Edgerton

[57] ABSTRACT

The compounds are trialkylphosphinegold(I)2,3,4,6-tetra-O-(N-loweralkylcarbamoyl)-1-thio-β-D-glucopyranosides which have antiarthritic activity and, in particular, are of use in the treatment of rheumatoid arthritis.

6 Claims, No Drawings

TRIALKYLPHOSPHINEGOLD(I)-LOWER ALKYL CARBAMOYL GLUCOPYRANOSIDES

This invention relates to new trialkylphosphinegold(I) 2,3,4,6-tetra-O-(N-loweralkylcarbamoyl)-1-thio-β-D-glucopyranosides. These compounds have antiarthritic activity and, in particular, are of use in the treatment of rheumatoid arthritis.

The compounds of this invention are represented by the following formula:

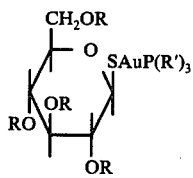

FORMULA I in which:

R is CO—NH-lower alkyl and

R' is straight or branched lower alkyl.

The term "lower alkyl" used in the definition of R and R' in Formula I denotes groups having 1–4 carbon atoms.

Preferably, in Formula I, R is CO—NH—CH$_3$. Also, preferably in Formula I, R' is ethyl.

A particular compound of this invention is represented by Formula I in which R is CO—NH—CH$_3$ and R' is ethyl, said compound being S-triethylphosphinegold(I) 2,3,4,6-tetra-O-(N-methylcarbamoyl)-1-thio-β-D-glucopyranoside.

The compounds of this invention are prepared by the reaction of an S-trialkylphosphinegold(I) 1-thio-β-D glucopyranoside (prepared as described in U.S. Pat. No. 3,635,945) with a N-loweralkylcarbamoylating agent, such as lower alkyl isocyanate. The reaction may be conveniently carried out at room temperature using an excess of the lower alkyl isocyanate.

Alternatively, the compounds of this invention may be prepared by N-loweralkylcarbamoylating a 1-(protected)thio-β-D-glucopyranose, followed by removing the protecting group and treating with halo(-trialkylphosphine)gold(I). The protecting group on the 1-thio may be, for example, a trityl group which may be removed by treating with silver nitrate.

The compounds of this invention are useful in treatment of arthritis. This activity is demonstrated by the following test procedures.

Inhibition of adjuvant induced polyarthritis in rats, as measured by reduction of rat paw edema, is produced by compounds of this invention at daily oral doses of about 20 mg./kg. (calculated on gold content). In this test procedure, adjuvant arthritis in rats is produced by a single intradermal injection of 0.75 mg. of *Mycobacterium butyricum* suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to inhibit the development of either primary or secondary lesions of adjuvant arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg. to about 10 mg.

The method of producing antiarthritic activity by administering internally to an animal a compound of Formula I is also an object of this invention. The compounds of Formula I are administered in an amount sufficient to produce antiarthritic activity. The route of administration may be orally or parenterally, preferably orally. Advantageously, doses will be administered 1 or 2 times a day, with the daily dosage regimen being preferably from about 1 mg. to about 12 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The following examples are not limiting but are illustrative of the invention.

EXAMPLE 1

S-Triethylphosphinegold(I) 1-thio-β-D-glucopyranoside (5.2 g., 10.2 mmoles) was dissolved in 100 ml. of methyl isocyanate and the mixture was stirred at room temperature for four hours. The solution was evaporated at reduced pressure and the residue was chromatographed on silica with chloroform and methanol to give S-triethylphosphinegold(I) 2,3,4,6-tetra-O-(N-methylcarbamoyl)-1-thio-β-D-glucopyranoside.

Calculated for C$_{20}$H$_{38}$O$_9$N$_4$SAuP.H$_2$O C, 31.75; H, 5.33; N, 7.40; P, 4.09%; Found: C, 31.88; H, 5.04; N, 7.53; P, 4.18%.

IR (μ, nujol): 3.0 (NHCO), 5.8 (NCO), 13 (PEt)
NMR (δ, CHCl$_3$): 2.8 (NCH$_3$), 2.0–1.0 (PEt)

EXAMPLE 2

Alternatively, S-triethylphosphinegold(I) 2,3,4,6-tetra-O-(N-methylcarbamoyl)-1-thio-β-D-glucopyranoside may be prepared by the following procedure.

2,3,4,6-Tetra-O-acetyl-1-thio-β-D-glucopyranose, obtained from the hydrolysis of 29 g. of S-(2,3,4,6-tetra-O-acetyl-β-D-glucopyranosyl) thiopseudourea hydrobromide as in "Methods in Carbohydrate Chemistry", Vol. II, page 436 (Whistler and Wolfrom editors, Academic Press Inc., 1963), was dissolved in 250 ml. of chloroform and cooled to 0°–5° C. in an ice bath. Anhydrous pyridine (20 ml.) was added, followed by 27.9 g. of trityl chloride. The mixture was stirred overnight at ambient temperature and the organic solution was extracted with dilute hydrochloric acid, washed with 5% aqueous sodium carbonate solution and with brine, dried over magnesium sulfate and evaporated under reduced pressure. The residue was crystallized from ether, then recrystallized from benzene-cyclohexane to give S-trityl-2,3,4,6-tetra-O-acetyl-1-thio-β-D-glucopyranose, m.p. 177.5°–179.5° C.

S-Trityl-2,3,4,6-tetra-O-acetyl-1-thio-β-D-glucopyranose (21.0 g.) was suspended in 90 ml. of methanol, cooled to −15° C. and a solution of sodium methoxide prepared from 0.21 g. of sodium and 75 ml. of methanol was added. The mixture was stirred for 1 hour at room temperature, then concentrated under reduced pressure to give a solid residue. The residue was triturated with water, then chloroform was added. The mixture was filtered and concentrated to give a solid residue which was dried by azeotropic distillation in benzene. Further evaporation of solvent and drying in vacuo gave S-trityl-1-thio-β-D-glucopyranose.

S-Trityl-1-thio-β-D-glucopyranose (0.70 g., 1.6 mmole) is dissolved in 20 ml. of dry dimethylformamide. Methyl isocyanate (1.5 ml.) is added and the mixture is stirred for 1.5 hours at room temperature and for an additional two hours at 65° C. The solvent is evaporated at reduced pressure, the residue is triturated with water and neutralized to pH 4 with dilute hydrochloric acid. Extracting the organic materials into chloroform, evaporating the chloroform extract and chromatographing the residue on a silica column with ethyl acetate eluant gives S-trityl-2,3,4,6-tetra-O-(N-methylcarbamoyl)-1-thio-β-D-glucopyranose.

S-Trityl-2,3,4,6-tetra-O-(N-methylcarbamoyl)-1-thio-β-D-glucopyranose (5.1 mmole) is dissolved in 100 ml. of ether and 10 ml. of methanol is added. Silver nitrate (0.87 g.) is added with stirring at room temperature and the reaction is monitored for the disappearance of the starting material by thin layer chromatography. After 3.5 hours, 1.79 g. (5.1 mmole) of chloro(triethylphosphine)gold(I) is added and stirring is continued for 45 minutes. The mixture is filtered, the filtrate is evaporated and the residue is chromatographed on silica using ethyl acetate as eluant to give S-triethylphosphinegold(I) 2,3,4,6-tetra-O-(N-methyl-carbamoyl)-1-thio-β-D-glucopyranoside.

EXAMPLE 3

Using ethyl isocyanate in place of methyl isocyanate in the procedure of Example 1, the product is S-triethylphosphinegold(I) 2,3,4,6-tetra-O-(N-ethylcarbamoyl)-1-thio-β-D-glucopyranoside.

Similarly using propyl isocyanate and butyl isocyanate, the products are S-triethylphosphinegold(I) 2,3,4,6-tetra-O-(N-propylcarbamoyl)-1-thio-β-D-glucopyranoside and S-triethylphosphinegold(I) 2,3,4,6-tetra-O-(N-butylcarbamoyl)-1-thio-β-D-glucopyranoside, respectively.

EXAMPLE 4

By the procedure of Example 1 using, in place of S-triethylphosphinegold(I) 1-thio-β-D-glucopyranoside, 10.2 mmoles of the following:

S-trimethylphosphinegold(I) 1-thio-β-D-glucopyranoside

S-tri-n-butylphosphinegold(I) 1-thio-β-D-glucopyranoside

S-triisopropylphosphinegold(I) 1-thio-β-D-glucopyranoside the following products are prepared:

S-trimethylphosphinegold(I) 2,3,4,6-tetra-O-(N-methylcarbamoyl)-1-thio-β-D-glucopyranoside S-tri-n-butylphosphinegold(I) 2,3,4,6-tetra-O-(N-methylcarbamoyl)-1-thio-β-D-glucopyranoside S-triisopropylphosphinegold(I) 2,3,4,6-tetra-O-(N-methylcarbamoyl)-1-thio-β-D-glucopyranoside.

EXAMPLE 5

| Ingredients | Amounts |
|---|---|
| S-triethylphosphinegold(I) 2,3,4,6-tetra-O-(N-methylcarbamoyl)-1-thio-β-D-glucopyranoside | 5 mg. |
| magnesium stearate | 5 mg. |
| lactose | 150 mg. |

The above ingredients are screened, mixed and filled into a hard gelatin capsule.

The capsules are administered orally to a subject in need of antiarthritic treatment in amounts within the daily dose range given hereabove.

Similarly, the other gold compounds of Formula I may be formulated into capsules by the procedure of Example 5.

Other pharmaceutical compositions containing, as the active ingredient, a compound of Formula I are prepared by standard procedures.

What is claimed is:

1. A compound of the formula:

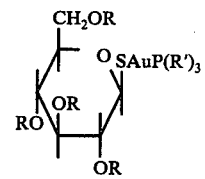

in which:
R is CO—NH-lower alkyl and
R' is straight or branched lower alkyl.

2. A compound of claim 1 in which R is CO—NH—CH$_3$.

3. A compound of claim 1 in which R' is ethyl.

4. A compound of claim 1, said compound being S-triethylphosphinegold(I) 2,3,4,6-tetra-O-(N-methylcarbamoyl)-1-thio-β-D-glucopyranoside.

5. A pharmaceutical composition having antiarthritic activity, in dosage unit form, comprising a pharmaceutical carrier and a compound of claim 1.

6. A method of producing antiarthritic activity which comprises administering internally to an animal a compound of claim 1.

* * * * *